US005769089A

United States Patent [19]

Hand et al.

[11] Patent Number: 5,769,089
[45] Date of Patent: Jun. 23, 1998

[54] EXTERNAL NASAL SPLINT

[75] Inventors: Timothy F. Hand; Anthony Manganaro, both of Annapolis Junction, Md.; Michael Chen, Taipei, Taiwan

[73] Assignee: Hanover Corporation, Annapolis Junction, Md.

[21] Appl. No.: 524,959

[22] Filed: Sep. 8, 1995

[51] Int. Cl.$^6$ ..................................................... A61F 9/00
[52] U.S. Cl. ......................... 128/858; 128/848; 606/199; 602/902
[58] Field of Search ..................... 128/846, 858, 128/848, 200.24, 204.12, 207.18, DIG. 26, 912; 602/12, 16, 17, 60, 74, 902; 606/191, 196, 199, 201, 204.45

[56] References Cited

U.S. PATENT DOCUMENTS

| | | | |
|---|---|---|---|
| 3,426,751 | 2/1969 | Radewan | 606/204.45 |
| 5,022,389 | 6/1991 | Brennan | 606/204.45 |
| 5,476,091 | 12/1995 | Johnson | 606/204.45 |
| 5,533,499 | 7/1996 | Johnson | 606/204.45 |
| 5,533,503 | 7/1996 | Doubek | 606/204.45 |

*Primary Examiner*—Michael A. Brown
*Attorney, Agent, or Firm*—Sughrue, Mion, Zinn, Macpeak & Seas, PLLC

[57] ABSTRACT

Disclosed is an external nasal splint which is adapted so that it may be placed across the bridge of the human nose, where it facilitates breathing without irritating the skin across the bridge of the nose. The splint contains a planar sheet of flexible material which has in its length-wise direction a central portion and two opposing end portions. The planar sheet is joined to an adhesive layer which also has in its length-wise direction a central portion and two opposing end portions. The central portion and the two opposing end portions of the planar sheet have an upper surface which is not adhesive to human skin. The two opposing end portions of the adhesive layer have a lower surface which is adhesive to human skin, so that the two opposing end portions are capable of affixing the external nasal splint to the human nose for a typical period of use, for instance six to twenty-four hours; and the central portion has a lower surface which is not adhesive to human skin. Sandwiched between the planar sheet and the adhesive layer is a strip made of high density polyethylene. The plastic strip has a high flexural modulus and therefore has the effect of pulling the nostrils of the wearer outward for the period when the external nasal splint is worn. By pulling the nostrils outward, the external nasal splint widens the nasal passage, thereby improving breathing. Running along the lower surface of the adhesive layer and adhering to the lower surface of both opposing ends are covers.

14 Claims, 8 Drawing Sheets

EXTERNAL NASAL SPLINT

FIELD OF THE INVENTION

The present invention relates to a device which is suited to be applied to the nose of a human being, where it opens the nostrils and thereby facilitates breathing. By opening the nostrils, the device of the present invention alleviates certain types of breathing problems, such as snoring, without discomfort to the wearer. It also improves breathing during physical activity, even intense exercise.

BACKGROUND OF THE INVENTION

Because of the prevalence of breathing problems, such as snoring, many devices have been developed and tried. A number of these devices may tend to alleviate those problems, but unfortunately, they often cause discomfort because they must be worn for a prolonged period. Additionally, the nose, particularly the skin on the bridge of the nose, is a sensitive portion of the human body, increasing the potential for discomfort. As a result, these devices do not offer a satisfactory answer to breathing problems.

For instance, in some devices, an adhesive splint is applied to the wearer from one side of the nose across the bridge of the nose to the opposite side of the nose. The splint is affixed to the nose by an adhesive material running the full length of the splint. Unfortunately, the adhesive material which comes in contact with the skin on the bridge of the nose can cause discomfort, particularly when the splint is worn during sleep through the night. Additionally, because of adhesive across the entire bottom surface, adjustment of the splint to conform to the specific shape of the nose is difficult. Once this type of splint is brought in contact with the skin so that it adheres to the skin, its position on the nose cannot be adjusted without removing the splint from the nose and thereby diminishing the splint's capacity to adhere to the skin when applied again.

Accordingly, such devices are incapable of performing their essential function of facilitating breathing without causing discomfort for the wearer.

The present inventors have discovered that the objective of improving breathing can be fully achieved, without causing discomfort to the skin on the bridge of the nose.

SUMMARY OF THE INVENTION

The external nasal splint of the present invention is adapted so that it may be placed across the bridge of the human nose, where it facilitates breathing without irritating the skin across the bridge of the nose.

The external nasal splint comprises a planar sheet of flexible material having in its length-wise direction a central portion and two opposing end portions. The central portion and the two opposing end portions have an upper surface which is not adhesive to human skin.

The external nasal splint also comprises an adhesive layer which is substantially coextensive with the lower surface of the planar sheet and which has in its length-wise direction a central portion and two opposing end portions. The two opposing end portions of the adhesive layer have a lower surface which is adhesive to human skin, so that the two opposing end portions are capable of affixing the external nasal splint to the human nose for a typical period of use, for instance six to twenty-four hours; and the central portion of the adhesive has a lower surface which is either not adhesive to human skin or is covered by a soft coat which is not adhesive to human skin.

Sandwiched between the planar sheet and the adhesive layer is a strip made of high density polyethylene. The plastic strip has a high flexural modulus and therefore pulls the nostrils of the wearer outward while the external nasal splint is worn. By pulling the nostrils outward, the external nasal splint widens the nasal passage, thereby improving breathing and alleviating problems such as snoring.

Running along and adhering to the lower surface of the opposing ends of the adhesive layer are covers.

BRIEF DESCRIPTION OF THE DRAWINGS

FIG. 5C shows an embodiment of the present invention in which the opposing end portions 2,2 are such that the splint has a dog bone shape; FIG. 5D is a plan view of an embodiment of the present invention in which the planar shape of the splint is curved.

DETAILED DESCRIPTION OF THE INVENTION

Figure 1:
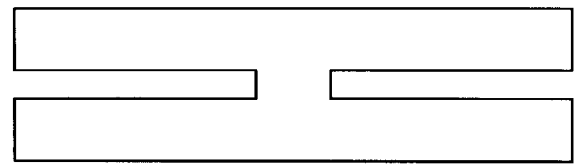
FIG. 1 is a plan view of an embodiment of a strip 1 for use in the external splint of the invention, which has an H-shape.

The planar sheet 10 may be made of a wide variety of flexible materials, particularly natural wood pulps or non-woven fabrics such as rayon. The outer surface of the planar sheet 10 is the visible portion of the splint when it is worn.

Attached to the lower surface of the planar sheet 10 is an adhesive layer. The adhesive layer 11 has two opposing ends portions 2,2, the lower surfaces of which adhere to human skin. The lower surface of the central portion of the adhesive layer 11 does not adhere to human skin or is covered with a soft coat 12 which does not adhere to human skin. In either event, the bridge of the nose is not exposed to an adhesive which may cause irritation. Sandwiched between the planar sheet 10 and the adhesive layer 11 is a plastic strip 1.

In a preferred embodiment of the present invention, the plastic strip 1 is 50 to 70 mm long, 11 to 15 mm wide, and 0.1 to 0.4 mm thick. In a more preferred embodiment, the plastic strip 1 is 55 to 65 mm long, 12 to 14 mm wide, and 0.2 to 0.3 mm thick. In the most preferred embodiment, the plastic strip 1 is about 60 mm long, about 11 mm wide, and about 0.25 mm thick.

In some embodiments of the invention, there are two plastic strips sandwiched between the planar sheet 10 and the adhesive layer 11 and running in the length-wise direction of the sheet and the layer. In other embodiments of the invention, there is only a single plastic strip 1 sandwiched between the planar sheet 10 and the adhesive layer 11 and running in the length-wise direction of the sheet and the layer.

Preferably, in those embodiments having a single plastic strip 1, the strip is H-shaped. It is believed that this H-shape permits the splint to conform more closely to the shape of the nose, while maintaining the basic bias of the strip which tends to open the nasal passage. More preferably, there is a gap 7 of 2 mm between the opposing bars 8,8 of the H-shaped strip, and the strip is about 4.5 mm wide, about 60 mm long and about 0.25 mm thick.

In the most preferred embodiments, the width at the outer ends of the opposing bars 8,8 of the H-shaped strip is greater than the width at the linking center 9, for instance, about 4.5 mm as opposed to 3.5 mm. It is believed that this structure enhances the flexural springback of the strip thereby expanding the nasal passage and promoting the objectives of the present invention.

Figure 6:
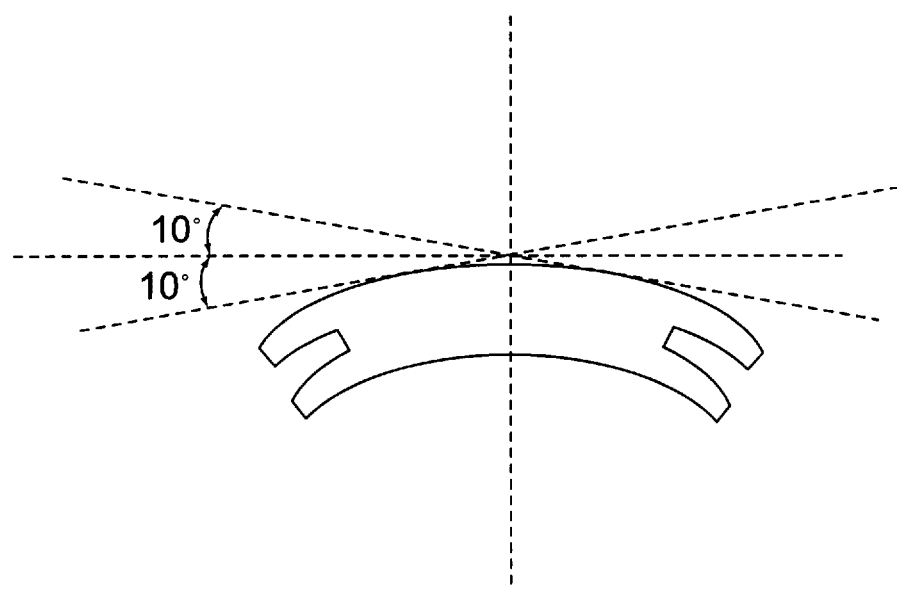
FIG. 6 is an X and Y drawing which shows how one measures the angle of curvature 4, using tangent lines, for those splints according to the present invention which are curved.

The H-shaped strip includes strips in which the connecting bar is quite narrow as in FIG. 1 and strips in which the connecting bar is quite wide as in FIG. 6.

The width of each opposing bar of the H-shaped strip is preferably 2 to 4 mm, more preferably 2.5 to 3.5 mm, most preferably about 3 mm. The ratio of the length of each opposing bar to the length of the linking center 9 is preferably 1:3 to 3:1, more preferably 1:2 to 2:1, most preferably about 1:1.

In some embodiments of the invention, the planar sheet and the adhesive layer are slightly longer than the plastic strip 1. For instance, the planar sheet 10 and the adhesive layer 11 may have a length of 60 mm and the plastic strip 1 a length of 56 mm, so that on both opposing ends, the planar sheet and the adhesive layer extend 2 mm beyond the plastic strip 1.

The plastic strip is preferably a high density polyethylene, polypropylene, polycarbonate or polyester. Polypropylene and polycarbonate are more preferred, and polyester is most preferred.

The preferred tensile strength of the plastic strip 1 is 24,000 to 30,000 psi, the more preferred tensile strength is 26,000 to 28,000 psi, and the most preferred tensile strength is about 27,000 psi. The tensile strength is measured according to ASTM D882-80.

The preferred flexural modulus of the plastic strip 1 is 40,000 to 46,000, the more preferred modulus 42,000 to 44,000, and the most preferred modulus about 42,500 to about 43,500, The flexural modulus is measured according to ASTM D882-80.

In a preferred embodiment, the cover is made of silicone and comprises two separate portions, one adhering to the adhesive of one of the two opposing end portions of the adhesive layer, and the other adhering to the adhesive of the other opposing end portion 2 of the adhesive layer 11.

Figure 4:
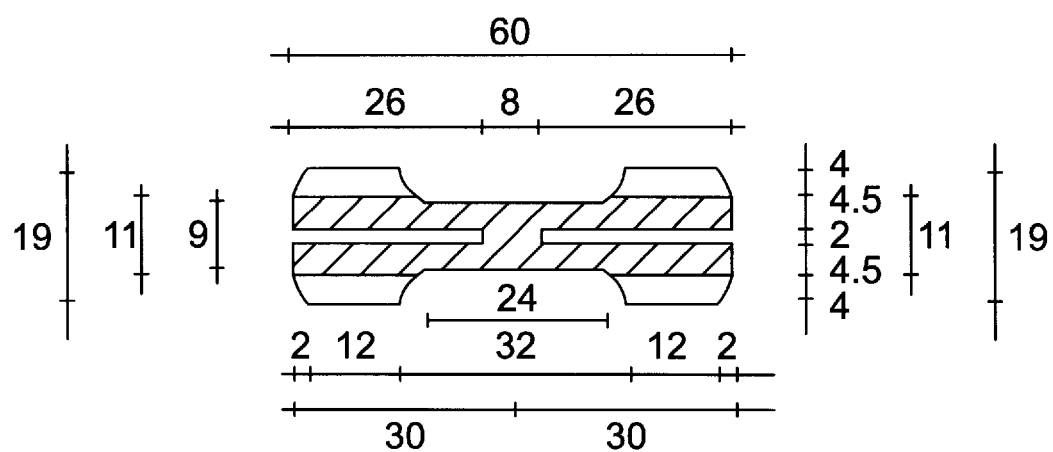
FIG. 4 is a plan view of a specific embodiment of the external splint 3 of the invention in which the opposing end portions 2,2 have the shape of octagons and in which the full splint has the shape of a dumbbell.

The two opposing end portions 2,2 of the splint may be in the shape of a circle, an axe, a square, a dog-bone, a hexagon, an octagon, or the feather portion 2,2 of an arrow. When the two opposing end portions 2,2 are in the shape of an octagon, the external nasal splint of the present invention is in the shape of a dumbbell. This dumbbell shape is shown in FIG. 4 in which the dimensions of the splint are given in millimeters. A hexagon shape is preferred, and an octagon shape is more preferred.

Figure 2:
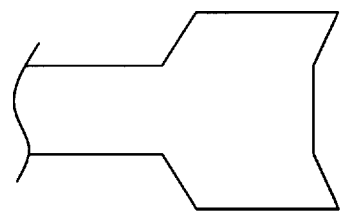
FIG. 2 is a plan view of the right side of an embodiment of the external splint of the invention in which the opposing end portion 2 has the shape of the feather of an arrow.
Figure 3:
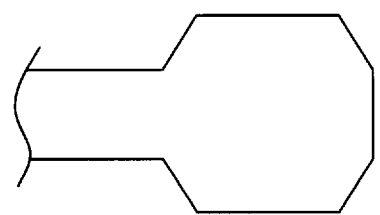
FIG. 3 is a plan view of the right side of an embodiment of the external splint of the invention in which the opposing end portion 2 has the shape of an octagon and in which the full splint and would have, if shown in its entirety, the shape of a dumbbell.

The octagon shape does not include any sharp points or residual tails, such as appear with the feather of an arrow shape. The octagon and arrow feather shapes are shown in FIGS. 2 and 3.

Figure 5A:
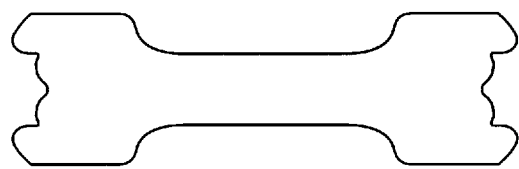
FIGS. 5A to 5D are plan views of different types of splints; the splints 3 of FIGS. 5A and 5B being in the prior art.
Figure 5B:
Figure 5C:
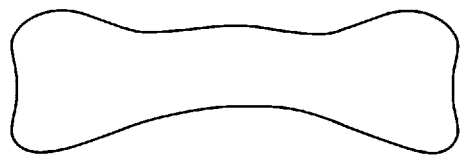
Figure 5D:
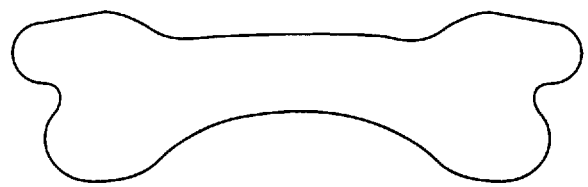
Figure 7A:
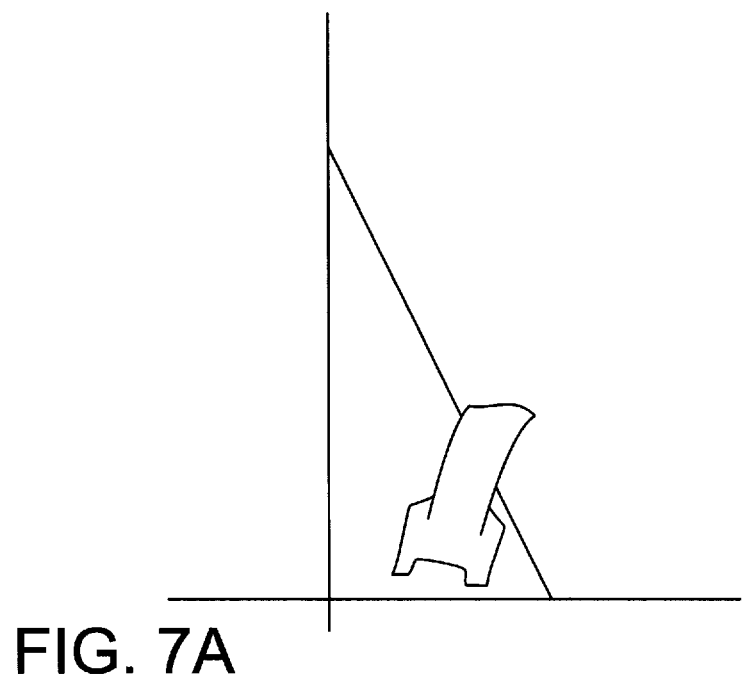
FIG. 7A is a side view of a straight splint as it is worn on the nose, in which the splint is not flush with the surface of the bridge of the nose 5 and tends to come in contact with the bridge only at the edge of the splint 6, thereby injuring that portion of the nose.
Figure 7B:
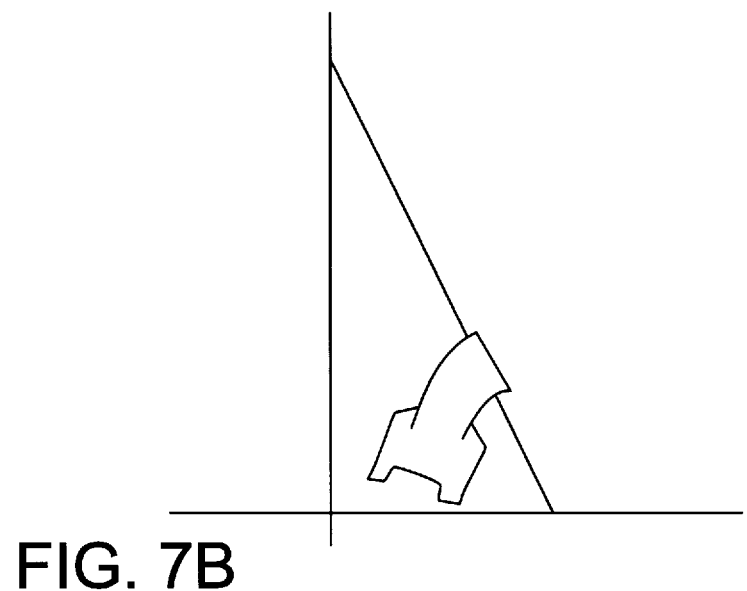
FIG. 7B is a side view of a curved splint which remains flush with the surface of the bridge of the nose 5 during use.
Figure 8A:
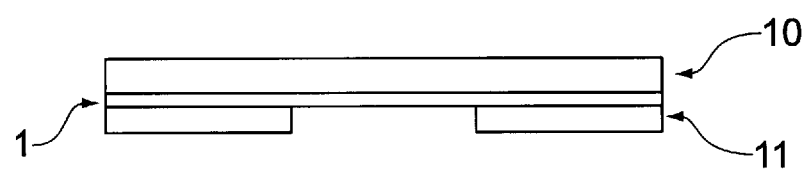
FIG. 8A is a cross-sectional view of the splint of the present invention, showing planar sheet 10, plastic strip 1 and adhesive layer 11.
Figure 8B:
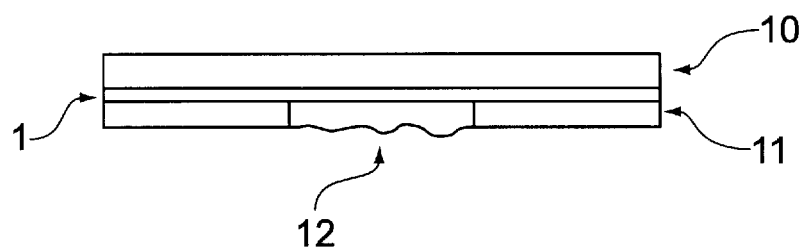
FIG. 8B is a cross-sectional view of the splint of the present invention, showing planar sheet 10, strip 1 and soft coat 12/adhesive layer 11.

In certain preferred embodiments of the present invention, the splint has a curved shape, such as in FIG. 5D, rather than a straight shape. It is believed that curvature permits the splint to remain flush with the surface of the bridge of the nose 5 during use as shown in FIG. 7B. If a splint is not flush with the surface of the bridge of the nose 5, it tends to come in contact with the bridge only at the edge of the splint, thereby injuring that portion of the nose, as shown in FIG. 7A.

Measurement of the angle of curvature is shown in FIG. 6. A curvature angle of 5°–30°, is preferred, 15°–25° more preferred, and about 20° most preferred.

A first protective backing or cover may be adhered to the adhesive of one of the two opposing end portions 2,2, and a second protective backing or cover may be adhered to the adhesive of other of the two opposing end portions 2,2. Alternatively, a single protective backing or cover may be adhered to the adhesive of both opposing end portions 2,2.

The splint of the present invention may also contain a scent which is either identifiable by the wearer as a pleasant smell or masks the smell of the remainder of the splint.

An arrow may be printed on the outer surface of the central portion of the planar sheet to indicate to the wearer how the splint is be applied.

EXAMPLE

In an example of the processes suitable for making an external nasal splint according to the present invention, a layer of fabric having the texture of cotton or rayon or a plastic serves as a backsupport. It is moved forward by a speed control driving motor which is suitable for a continuous input step. The upper surface of the fabric layer is covered with an adhesive substance, while the lower surface has no adhesive. A layer of plastic sheet is moved by the above driving system in a simultaneous input step, over the adhesive surface of the backsupport. A cut mold is used to form an H-shaped plastic strip from the plastic sheet, and the H-shaped plastic strip is applied to the adhesive surface of the backsupport.

An intermediate layer is formed, which is adhesive on both sides thereof. The intermediate layer is driven forward by the above driving system and is placed over the H-shaped plastic strip. The intermediate layer may be an acrylate or other polymer or a mixture thereof.

An upper layer having a fabric texture of spun-laced or thermobonding polyester is moved by the above driving system over the intermediate layer and bonded thereto. On the outer surface of the upper layer is adhesive to human skin in the opposing portions of the intermediate layer which correspond to the sides of the nostrils, but not on the central portion of the intermediate layer which corresponds to the bridge of the nose. In an alternative structure, there are two upper layers which respectively cover the end portions of the intermediate layer, but do not cover the central portion of the intermediate layer which corresponds to the bridge of the nose.

Two silicone liners which function as protective layers are respectively applied to the two adhesive portions of the outer surface of the upper layer or to the adhesive outer surface of the two upper layers.

The assembled layers and liner are then subjected to a form cutter to impart to the splint its desired shape, for instance a dumbbell shape.

The shaped splint may then be packaged according to methods well known in the art.

We therefore claim:

1. An external nasal splint adapted to be placed across the bridge of the human nose, said splint comprising
    a planar sheet of flexible material comprising in its length-wise direction a central portion and two opposing end portions,
    an adhesive layer substantially coextensive with and adhering to the lower surface of the planar sheet and comprising in its length-wise direction a central portion and two opposing end portions,
    a plastic strip sandwiched between the planar sheet and the adhesive layer and running in the length-wise direction of the planar sheet and adhesive layer,
    wherein the central portion and the two opposing end portions of the planar sheet have an upper surface which is not adhesive to human skin,
    wherein the two opposing end portions of the adhesive layer have a lower surface which is adhesive to human skin such that the two opposing end portions of the adhesive layer are capable of affixing the nostril splint to the human nose, and
    wherein the central portion of the adhesive layer has a lower surface which is covered by a soft coat which is not adhesive to human skin,
    and a cover adhering to the lower surface of the two opposing end portions of the adhesive layer.

2. The external nasal splint of claim 1, wherein the two opposing end portions of the planar sheet and the adhesive layer are wider in their transverse direction than the central portion in its transverse direction.

3. The external nasal splint of claim 2, wherein the width of the splint in the transverse direction tapers from the two opposing end portions to the central portion of the planar sheet and the adhesive layer.

4. The external nasal splint of claim 1, wherein the external nasal splint is in the shape of a dumbbell.

5. The external nasal splint of claim 1, wherein attached to or embedded within the central portion is an identifiable scent.

6. The external nasal splint of claim 1, wherein the splint further comprises a first protective backing adhering to the adhesive of one of the two opposing end portions, and a second protective backing adhering to the adhesive of other of the two opposing end portions.

7. The external nasal splint of claim 1, wherein there are two plastic strips sandwiched between the planar sheet and the adhesive layer, and running in the length-wise direction of the planar sheet and the adhesive layer.

8. The external nasal splint of claim 1, wherein there is a single plastic strip sandwiched between the planar sheet and the adhesive layer, and running in the length-wise direction of the planar sheet and the adhesive layer.

9. The external nasal splint of claim 1, wherein the single plastic strip is H-shaped.

10. The external nasal splint of claim 1, wherein the central portion of the adhesive layer has a lower surface which is not adhesive to human skin.

11. The external nasal splint of claim 1, wherein the central portion of the adhesive layer has a lower surface which is covered by a soft coat.

12. The external nasal splint of claim 1, wherein the external nasal splint is curved and has an angle of curvature of 5°–30°.

13. The external nasal splint of claim 1, wherein the external nasal splint is curved and has an angle of curvature of 15°–25°.

14. The external nasal splint of claim 1, wherein the external nasal splint is curved and has an angle of curvature of about 20°.

* * * * *